US005633504A

United States Patent [19]
Collins et al.

[11] Patent Number: 5,633,504
[45] Date of Patent: May 27, 1997

[54] INSPECTION OF OPTICAL COMPONENTS

[75] Inventors: Theresa A. Collins, Park Ridge; L. Lawrence Chapoy, Barrington, both of Ill.

[73] Assignee: Wesley-Jessen Corporation, Chicago, Ill.

[21] Appl. No.: 413,327

[22] Filed: Mar. 30, 1995

[51] Int. Cl.$^6$ .................................................. G01N 21/64
[52] U.S. Cl. ........................................ 250/461.1; 250/459.1
[58] Field of Search ............................. 250/461.1, 459.1, 250/458.1

[56] References Cited

U.S. PATENT DOCUMENTS

| | | | |
|---|---|---|---|
| 1,464,999 | 8/1923 | Pyser | 250/461.1 |
| 3,072,585 | 1/1963 | Milionis et al. | 260/22 |
| 3,399,173 | 8/1968 | Heller et al. | 260/47 |
| 4,362,943 | 12/1982 | Presby | 250/459.1 |
| 4,528,311 | 7/1985 | Beard et al. | 524/91 |
| 4,716,234 | 12/1987 | Dunks et al. | 548/259 |
| 4,719,248 | 1/1988 | Bambury et al. | 523/108 |
| 4,868,251 | 9/1989 | Reich et al. | 525/479 |
| 5,303,023 | 4/1994 | Portney et al. | 356/124.5 |

FOREIGN PATENT DOCUMENTS

| | | |
|---|---|---|
| 88816/91 | 5/1992 | Australia . |
| 0 343 996 | 11/1989 | European Pat. Off. . |
| 3432002 | 3/1986 | Germany . |
| 2-257007 | 10/1990 | Japan . |
| 4-305144 | 10/1992 | Japan . |

*Primary Examiner*—Constantine Hannaher
*Attorney, Agent, or Firm*—Brinks Hofer Gilson & Lione

[57] ABSTRACT

A system and method for inspecting an optical component such as a hydrated contact lens in which the system includes an illuminator providing light to a receptacle supporting the optical component with a saline solution and an imaging sensing device such as an eye or a video camera detecting fluorescent light generated in the optical component or in some portion of the receptacle and blocked by the optical component. The system and method are particularly useful for inspecting optical components which have been produced to have ultraviolet-absorbing properties.

16 Claims, 2 Drawing Sheets

INSPECTION OF OPTICAL COMPONENTS

INTRODUCTION TO THE INVENTION

This invention relates to a system and method for the inspection of optical components. The optical components to be inspected may include, but are not limited to, ocular optical components such as contact lenses, eyeglasses, intraocular lenses and the like.

A principal objective of this invention is the inspection of contact lenses. Prior to the present invention, optical components such as contact lenses were often inspected manually, sometimes with the use of a projection-type device such as an optical comparator. Manual inspection systems requiring human intervention are not always practical for high-speed production because they are too slow, because human inspectors are prone to making biased judgments, and because inspection results among different inspectors may not correlate well.

A principal obstacle to automatic inspection and high-speed visual inspection has been the inability to produce high contrast images of optical components, including contact lenses, so that features such as cuts, edge imperfections, scratches, tears and chips can be readily detected and measured. In particular, it has been difficult to obtain high contrast images of entire optical components. As used herein, the term "features" includes both beneficial features such as certain topographical features of toric lenses and lens boundaries, as well as detrimental features such as scratches, tears and chips.

The principal difficulty in obtaining high contrast images of optical components such as contact lenses and eyeglass and other lenses is that they are usually transparent. Moreover, in the case of certain optical components, such as highly hydrated contact lenses called "hydrogels" which must remain immersed in a fluid such as a saline solution, the production of high contrast images involves a further complication. That is, the refractive indices for the optical component and the liquid solution may be so similar that boundaries between the two are nearly invisible. Images of the optical component are therefore inherently of low contrast.

Another difficulty in examining hydrogels is that they cannot easily be kept in a fixed position during examination and will move distances greater than the size of a small feature which the inspection process should detect. Therefore, it is important to obtain a high contrast image of an entire hydrogel so that an image can be captured by an imaging system in a fraction of a second.

SUMMARY OF THE INVENTION

The novel inspection system of the present invention is predicated upon the surprising discovery that despite the transparent nature of optical components, high contrast images of an optical component are produced by the use of fluorescence generated within or about the optical component. Typically, the image will be inherently be presented either as a light object against a "dark" field, or as a "dark" object against a light field, and defects will generally contrast highly with the image of the component.

A detailed description of the present invention is set forth below. However, the embodiments described herein are merely illustrative; further modifications and embodiments will be apparent to those having skill in the art.

DETAILED DESCRIPTION OF THE INVENTION

Figure 1:
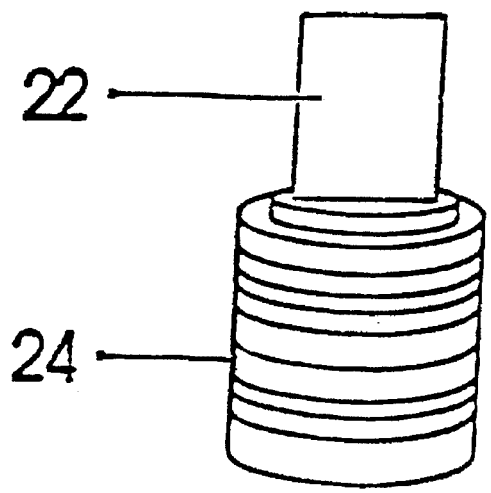
FIG. 1 is a schematic illustration of an automated inspection system of the invention.
Figure 1:
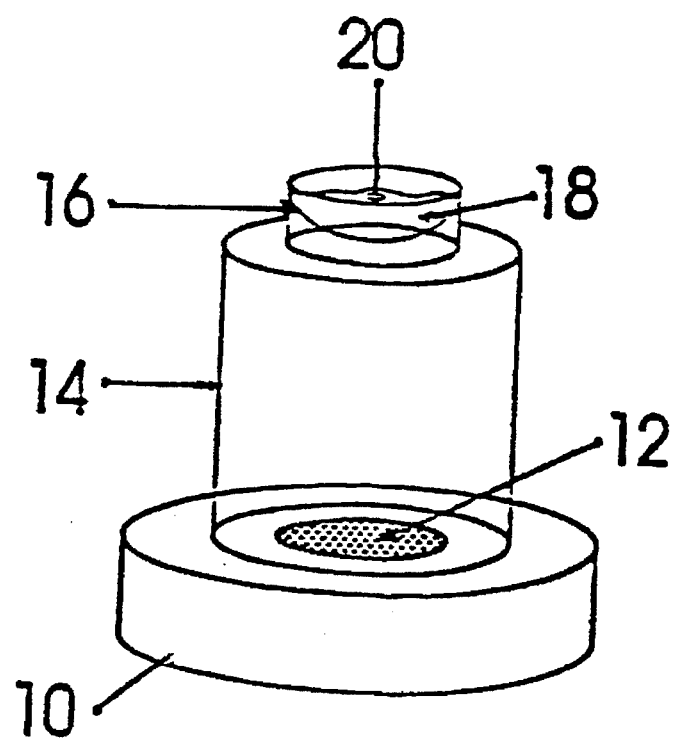

Referring to FIG. 1, showing a sample holder-illuminator (10) in a presently preferred automated inspection embodiment of the present invention, an illuminator (12), provides light to an inspection receptacle (16). The receptacle (16) contains a saline solution (18) for hydrating an optical component, here a contact lens (20). In addition to containing the solution (18) and the lens (20), the receptacle has been engineered to transmit light through the lens (20). Fluorescent light reaches means for sensing an image of the optical component. In a preferred embodiment, the image sensing means comprises a camera (22), preferably a video camera. An example of a suitable video camera is a SONY XC-77RR Charge Coupled Device (CCD) video camera. The camera is connected to a camera lens (24) having an entrance pupil (not shown).

Although the receptacle (16) is shown as being elevated above the illuminator (12) using a spacer (14), many embodiments of the invention will have the receptacle sitting directly above the illuminator.

In one embodiment, the only illumination light supplied to the system is light having wavelengths which will not be detected by the image sensing means, but will induce fluorescence in the lens, and the fluorescing lens therefore appears as a bright area against a dark field. Defects in the lens, including edge irregularities, appear as darker or black areas; very high contrast between the lens and its defects is obtained. In some instances, the illuminating wavelengths may be detectable by the image sensing means, giving a reduced contrast image.

In another embodiment, at least part of the lens-holding receptacle or support is made to fluoresce by exposure to illumination light having wavelengths preferably outside the range which is detectable by the detection system being used (a video camera, the eye, etc.) and which do not induce lens fluorescence. The lens will appear as a dark body, surrounded by light, and defects will appear as light areas within the lens.

Light of any wavelength can be used to produce the desired fluorescence, keeping in mind that different fluorescing entities have differing requirements for excitation energies. It is generally the case that ultraviolet light will be considered convenient for this purpose, since many materials exhibit visible fluorescence when they are exposed to ultraviolet wavelengths. Further, much existing imaging equipment responds to visible light and not to ultraviolet wavelengths. However, a large number of materials of interest exhibit fluorescence in the visible spectrum when exposed to lower-wavelength visible light, and can be used in the present invention under such conditions. When using excitation light having wavelengths which can be readily detected by the imaging equipment, it typically will be beneficial to use appropriate filters or introduce the excitation beam at an appropriate angle to the fluorescent light axis, to limit the intensity of undesired illumination wavelengths which reach the detector of the imaging equipment and thereby improve contrast.

A presently preferred video camera (22) for use in the present invention contains a ⅔ inch CCD array (not shown) of individual sensors, each of which is capable of transducing light energy into electrical energy. The CCD array has 493 horizontal rows of individual sensors. Each row has 768 individual sensors. Thus, the total array contains 378,264 individual sensors. The camera generates 30 frames or images per second. The camera may be connected to a video monitor to view the image of the optical component, or be connected to an electronic imaging system which can analyze automatically image electrical signals received from camera (22). Many other cameras are suitable for the practice of the invention.

A preferred embodiment of the present invention further comprises an electronic imaging system (not shown) for analyzing image signals received from the camera (22), wherein the electronic imaging system comprises means for detecting in the image signals an "image property" corresponding to a given feature appearing in the optical component. For instance, where an 8-bit electronic imaging system is used (as for example one containing an EPIX Model 10 Imaging Board), an "image property", as the term is used herein can constitute a value in the range from 0 to 255 which is assigned to each gray level in an image.

Of course, it is not necessary to use any expensive, complicated automation system for enhanced inspections using the present invention. Any fluorescent system in which the excitation light is excluded or diminished in detectable intensity will provide high contrast between the optical component and the background, facilitating inspections with the unaided eye, any type of magnifying device such as a microscope, a device which projects a magnified image onto a screen, and the like.

Figure 2:
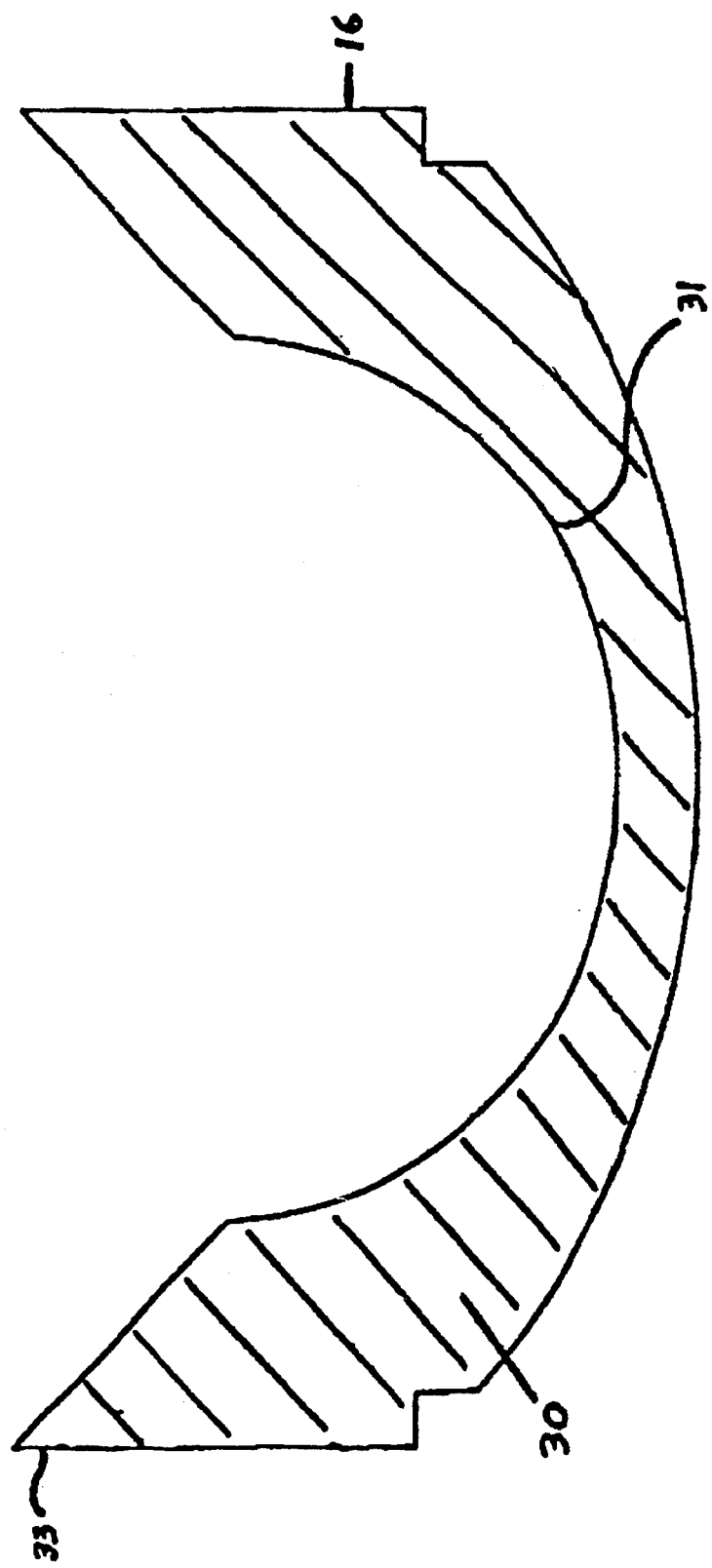
FIG. 2 is a cross-sectional view of a receptacle for inspecting a contact lens using the invention.

The present invention provides, in one embodiment, receptacle (16) for holding an optical component in position during inspection. Referring to FIG. 2, the receptacle (16) preferred in the present invention for holding a hydrated contact lens comprises a bottom portion (30) having a concave inner surface (31) for utilizing the force of gravity to hold the lens in the center of the receptacle (16). Preferably, the concave curve of the inner surface (31) has a steep radius of curvature in order to maximize the force of gravity upon the lens positioned therein. (Note: the lens is not shown in FIG. 2). The radius of curvature of the inner surface (31) is preferably equal to or greater than the radius of curvature of the particular surface of the lens which is intended to be closest to the receptacle's concave inner surface (31). Basically, the radius of curvature of the receptacle's concave inner surface (31) is chosen to be as steep as possible to maximize the centering ability of the receptacle while being shallow enough to maintain center contact with the lens under inspection. This minimizes the distance that the lens (22, FIG. 1) can move in $\frac{1}{30}$ second, the time typically required to "freeze" an image of an optical component with a device such as a video camera. In order to obtain reliable feature detection, it is highly desirable to restrict the distance a hydrogel can move in one frame time (i.e. $\frac{1}{30}$ second) to a distance less than the smallest size feature which must be detected.

When the receptacle of the present invention is used in connection with this invention's novel inspection system, the receptacle's bottom portion (30) is typically made of a transparent material, such as glass, clear polycarbonate or polystyrene plastic, or an acrylic material, such as polymethmethacrylate.

Under certain circumstances, such as the inspection of hydrated contact lenses, it is desirable to keep the lens immersed in a liquid solution, especially a saline solution. Under such circumstances, the receptacle of the present invention can be constructed to hold a liquid solution. With reference to FIG. 2, this can be accomplished by providing a "water-tight" receptacle wherein side walls (33) of the receptacle's bottom portion (30) extend upward for a sufficient height such that liquid will be contained within the receptacle without leaking or spilling.

It should be noted that contact and intraocular lenses, and many other optical components, may be inspected in a non-hydrated or dry state. In this case, the holder needs only to immobilize the lens, preferably in or near the center of the holder, and therefore can be of a more simple design.

With regard to a preferred alignment of the system of the present invention, the image sensing means is optically aligned with the clear receptacle (16) and the optical component to be inspected (20) such that the optical axes of each are coaxial.

Optical components to be inspected with the above-described system are those which fluoresce when irradiated with an appropriate source, or are non-fluorescing optical components which are contained within or on a fluorescing holder, support or container. Typically, the irradiating light will be ultraviolet light and the fluorescence will be in the visible range of wavelengths; such conditions are frequently preferred, since the image sensing means can be selected to not respond to ultraviolet light and will show the optical component's image as a light area on a black background. However, it is possible to use higher irradiation wavelengths and interpose filters between the optical component and the image sensing means to prevent undesirable amounts of the light source energy from entering the light detector.

Most ultraviolet-absorbing materials exhibit fluorescence. In the case of contact and intraocular lenses, ultraviolet absorption is obtained by incorporating into or onto the lenses a chemical material such as a substituted benzotriazole, a benzophenone, a compound such as divinyl stilbene or a compound having a triazine moiety.

Useful benzotriazole compounds for lenses to be inspected by the system and method of this invention include those having the formula:

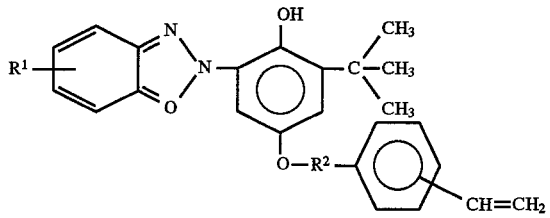

wherein $R^1$ is a halogen or $C_1$–$C_6$ straight or branched chain alkoxy group; and $R^2$ is a —(CH$_2$)$_3$O—, —(CH$_2$)$_2$O—, —CH(CH$_3$)CH$_2$O—, —CH$_2$CH(CH$_3$)O—, —(CH$_2$)$_3$OCH$_2$—, —(CH$_2$)$_2$OCH$_2$—, —CH(CH$_3$)CH$_2$OCH$_2$—, or —CH$_2$CH(CH$_3$)OCH$_2$—group.

Other useful benzotriazoles are described in the following U.S. Pat. No. : 3,072,585 to Milionis et al.; U.S. Pat. No. 3,399,173 to Heller et al.; U.S. Pat. No. 4,716,234 to Dunks et al.; U.S. Pat. No. 4,719,248 to Bambury et al.; U.S. Pat. No. 4,528,311 to Beard et al.; and in European Patent Application 0 343 996 A3 (Alcon Laboratories, Inc.).

Useful benzotriazoles and substituted 2-hydroxybenzophenones are also described in U.S. Pat. No. 4,868,251 to Reich et al., as is their use in optical components made from silicone elastomers.

The foregoing discussion has emphasized fully or partially automated inspection systems for optical components. For economic reasons, such systems are preferred when components are being produced at high rates and satisfactory inspections can be made by automated equipment. However, in many instances it will be useful to manually inspect each, or a certain percentage, of optical components on a production line using the unaided eye or with the eye assisted by some type of magnification device; the present invention facilitates manual inspections, by providing the presentation of a high-contrast image of the component against a background.

The invention has been described and exemplified using certain presently preferred embodiments, but is not to be limited thereto, the scope of the invention being defined solely by the appended claims.

What is claimed is:

1. A method for inspecting a contact lens or intraocular lens, comprising irradiating the lens with radiation to induce fluorescence in or about the lens, detecting an image of the fluorescing area and analyzing the image for defects.

2. The method of claim 1, wherein the lens is a hydrated contact lens.

3. The method of claim 1, wherein the radiation is ultraviolet light.

4. The method of claim 1, wherein the image is detected by means comprising a video camera.

5. The method of claim 1, wherein the image is detected and analyzed using the eye, either unaided or in conjunction with a magnifying device.

6. The method of claim 1, wherein the radiation is visible light, at least a portion of which is excluded from the image.

7. The method according to claim 1, wherein the analyzing the image for defects comprises the step of nondestructively testing for edge irregularities of said lens.

8. The method according to claim 1, wherein the analyzing the image for defects comprises the step of nondestructively testing for cuts, scratches or tears of said lens.

9. A method for inspecting a contact lens or intraocular lens, comprising irradiating a holder or support for said lens with radiation to induce fluorescence in or about the lens, detecting an image of a dark portion of the fluorescing area and analyzing the image for defects.

10. The method of claim 9, wherein the lens is a hydrated contact lens.

11. The method of claim 9, wherein the radiation is ultraviolet light.

12. The method of claim 9, wherein the image is detected by means comprising a video camera.

13. The method of claim 9, wherein the image is detected and analyzed using the eye, either unaided or in conjunction with a magnifying device.

14. The method of claim 9, wherein the radiation is visible light, at least a portion of which is excluded from the image.

15. The method according to claim 9, wherein the analyzing the image for defects comprises the step of nondestructively testing for edge irregularities of said lens.

16. The method according to claim 9, wherein the analyzing the image for defects comprises the step of nondestructively testing for cuts, scratches or tears of said lens.

* * * * *